(12) United States Patent
Meyer et al.

(10) Patent No.: US 12,121,615 B2
(45) Date of Patent: Oct. 22, 2024

(54) GEL TYPE PHARMACEUTICAL COMPOSITION FOR TREATING/PREVENTING AN INFECTION

(71) Applicant: ATLANGRAM, Nantes (FR)

(72) Inventors: Olivier Meyer, Angers (FR); Amokrane Reghal, Savenay (FR)

(73) Assignee: Amokrane Reghal, Savenay (FR)

( * ) Notice: Subject to any disclaimer, the term of this patent is extended or adjusted under 35 U.S.C. 154(b) by 789 days.

(21) Appl. No.: 17/267,541

(22) PCT Filed: Jan. 8, 2020

(86) PCT No.: PCT/EP2020/050253
§ 371 (c)(1),
(2) Date: Feb. 10, 2021

(87) PCT Pub. No.: WO2020/144201
PCT Pub. Date: Jul. 16, 2020

(65) Prior Publication Data
US 2021/0315828 A1      Oct. 14, 2021

(30) Foreign Application Priority Data

Jan. 8, 2019 (EP) .................................. 19305019

(51) Int. Cl.
*A61K 9/51* (2006.01)
*A61K 38/12* (2006.01)
*A61P 19/00* (2006.01)
*A61P 31/04* (2006.01)

(52) U.S. Cl.
CPC .......... *A61K 9/5123* (2013.01); *A61K 9/5153* (2013.01); *A61K 9/5161* (2013.01); *A61K 38/12* (2013.01); *A61P 19/00* (2018.01); *A61P 31/04* (2018.01)

(58) Field of Classification Search
None
See application file for complete search history.

(56) References Cited

U.S. PATENT DOCUMENTS

| 2013/0034612 A1* | 2/2013 | Mallard | A61P 17/08 |
| | | | 264/4.1 |
| 2015/0125520 A1 | 5/2015 | Mallard | |
| 2021/0315828 A1 | 10/2021 | Meyer et al. | |

FOREIGN PATENT DOCUMENTS

| EP | 1 265 698 B1 | 6/2004 |
| EP | 3679928 A1 | 7/2020 |
| EP | 3908265 A1 | 11/2021 |
| FR | 2 840 532 A1 | 12/2003 |
| FR | 3 017 294 A1 | 8/2015 |
| IL | 284669 A | 8/2021 |
| WO | 0164328 A1 | 9/2001 |
| WO | 2008/043973 A1 | 4/2008 |
| WO | 2009001019 A2 | 12/2008 |
| WO | 2009004214 A2 | 1/2009 |
| WO | 2010067037 A1 | 6/2010 |
| WO | 2012/114201 A1 | 8/2012 |
| WO | 2015118496 A1 | 8/2015 |
| WO | 2018091895 A1 | 5/2018 |

OTHER PUBLICATIONS

Reghal et al. (WO2015118496A4 Machine Translation) (Year: 2015).*
Office Action in Chinese Application No. 202080005348.3, mailed Sep. 15, 2022.
Chong Li et al., "Preparation and characterization of flexible nanoliposomes loaded with daptomycin, a novel antibiotic, for topical skin therapy", International Journal of Nanomedicine, Mar. 1, 2023, p. 1285.
J. D. Alder, "Daptomycin, a new drug class for the treatment of gram-positive infections", Drugs of Today, vol. 41, No. 2, Jan. 1, 2005, p. 81.
Cédric Jacqueline et al., "Management of MRSA/GISA, VISA Endocarditis", Current Infections Disease Reports, vol. 15, No. 4, Jun. 12, 2013, pp. 339-334.
M. Lefebvre et al., "Efficacy of daptomycin combined with rifampicin for the treatment of experimental meticillin-resistant *Staphylococcus aureus* (MRSA) acute osteomyelitis", International Journal of Antimicrobial Agents, vol. 36, No. 6, Dec. 1, 2010, pp. 542-544.
Jaleh Varshosaz et al., "Lipid Nanocapsule-Based Gels for Enhancement of Transdermal Delivery of Ketorolac Tromethamine", Journal of Drug Delivery; vol. 22, No. 6, Jan. 1, 2011.
International Search Report & Written Opinion in Corresponding PCT Application No. PCT/EP2020/050253 mailed Mar. 18, 2020. 12 pages.

* cited by examiner

Primary Examiner — Robert A Wax
Assistant Examiner — Quanglong N Truong
(74) Attorney, Agent, or Firm — THE MARBURY LAW GROUP, PLLC

(57) ABSTRACT

The present invention relates to a pharmaceutical composition stabilized in a gelled state at at least a temperature varying from 15° C. to 40° C., comprising at least one aqueous phase gelled with at least one hydrophilic polymeric gelling agent, lipid nanocapsules comprising a liquid or semi-liquid lipid core at room temperature enveloped in a lipid envelope which is solid at room temperature, said gelled aqueous phase and nanocapsules containing at least one antibiotic, identical or different, the antibiotic in said aqueous phase being present there in the form of a solute.

13 Claims, 3 Drawing Sheets

GEL TYPE PHARMACEUTICAL COMPOSITION FOR TREATING/PREVENTING AN INFECTION

CROSS-REFERENCE TO RELATED PATENT APPLICATIONS

Figure 1:
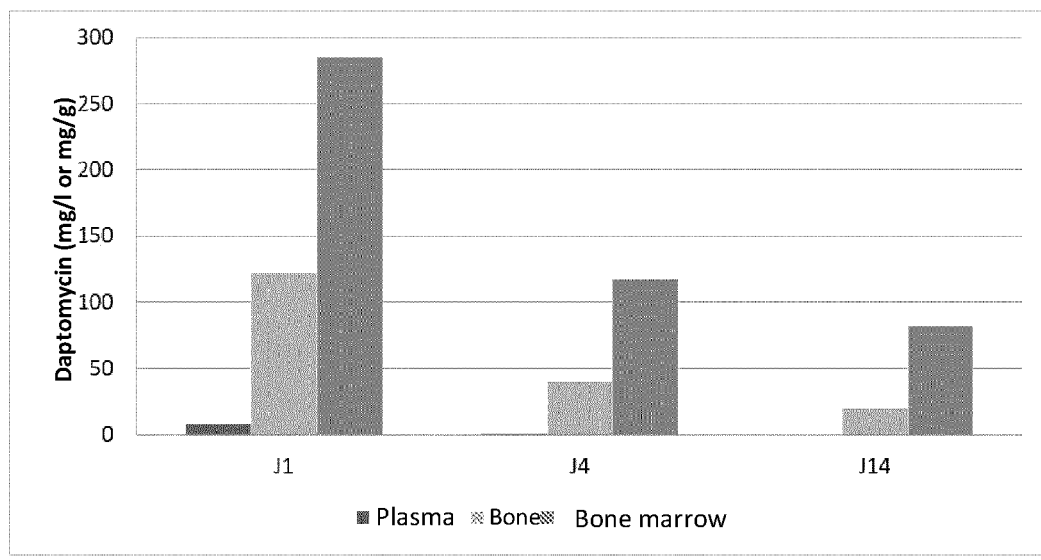

This application is a U.S. National Stage Application under 35 U.S.C. § 371 of International Patent Application No. PCT/EP2020/050253, filed Jan. 8, 2020, which claims the benefit of priority of European Patent Application number 19305019.2 filed Jan. 8, 2019, both of which are incorporated by reference in their entireties. The International Application was published on Jul. 16, 2020, as International Publication No. WO 2020/144201 A1.

The present invention relates to novel pharmaceutical compositions, suitable for localized administration and controlled in terms of duration, with active ingredients such as antibiotics, as well as corresponding medical devices. It also relates to their therapeutic uses for treating or preventing an infection, in particular bacterial and in particular osteoarticular bacterial infections.

Antibiotics remain the most widely used active ingredients today to treat bacterial infections. However, in certain cases, their implementation has not yet proved to be completely satisfactory, in particular in terms of efficacy, spectrum of action and bioavailability.

In addition, antibiotics are usually administered to the patient orally or parenterally. However, in the case of specifically localized bacterial infections, this mode of administration may not be effective enough, taking into account a lack of optimal diffusion at the infection site. In particular, this difficulty concerns infections affecting the bones, joints, or infections developing at an implanted medical device, such as an implant or a prosthesis, and for which it is often necessary to perform additional surgery to clear the infection.

Consequently, the development of galenic formulations dedicated to the administration of active ingredients to treat infections, in particular bacterial, which are more efficient in terms of pharmacokinetic and pharmacodynamic properties and of targeting, is of great interest.

It is already known from FR3017294 to convey antibiotics such as daptomycin, vancomycin and rifampicin in lipid nanocapsules. This galenic form turns out to be particularly advantageous from the standpoint of bioavailability and therefore makes it possible to use smaller doses of antibiotics for an efficacy at least equivalent to that of the other forms. However, these lipid nanocapsules only tolerate a low level of antibiotic load, namely a level of less than 50 mg/ml of suspension. Indeed, beyond a certain concentration of antibiotic, the surfactant properties of the latter disturb the formation of the particles. Moreover, these nanocapsules do not make it possible to modulate over time a release profile of the active ingredient. Most often, the release is rapid and/or non-linear.

Finally, the administration of these nanocapsules is essentially recommended parenterally. Consequently, it is still difficult to target bacterial infection locally such as an osteoarticular bacterial infection.

However, osteoarticular infections are serious pathologies that affect a bone and/or a joint. They can occur spontaneously following sepsis, after a deep wound or an open fracture for example, or else constitute a surgical complication, such as for example the placement of an implant, prosthesis, plate or screw, what are commonly called infections on foreign material (or implanted medical device).

These bone and joint infections are therefore still difficult to treat today, especially in the case of infections on joint prostheses, because the bacteria also bind to the materials of the implants, making antibiotics ineffective and requiring surgery to control or clear the infection.

It should also be emphasized that the treatment of osteoarticular infections can be particularly trying for the patient because of the heaviness and duration of the antibiotic therapy and too often the need to resort to an appropriate prior surgery in order to control or reabsorb the infection followed most often by a post-operative period of rehabilitation.

The present invention is specifically aimed at providing a novel galenic form for antibiotics making it possible to overcome the aforementioned shortcomings.

In particular, the present invention provides a pharmaceutical composition effective for locally delivering an effective amount of at least one therapeutic active agent, in particular an antibiotic, and in particular directly at the site of bacterial infection.

The present invention aims in particular to provide a pharmaceutical composition suitable for a targeted administration of at least one therapeutic active agent, in particular an antibiotic for treating a bacterial infection affecting the bones, the joints, or developing at an implanted medical device, such as an implant or prosthesis.

In particular, the present invention provides a pharmaceutical composition effective for locally treating a bacterial osteoarticular infection.

The present invention also aims to provide an effective pharmaceutical composition for delivering in a controlled manner and in particular for a prolonged period of time the active ingredient which it contains so that the medication is as effective as possible and has a prolonged duration of action.

Thus, the present invention mainly relates to a pharmaceutical composition stabilized in a gelled state at at least a temperature varying from 15° C. to 40° C., comprising at least:

an aqueous phase gelled with at least one hydrophilic polymeric gelling agent, lipid nanocapsules containing a liquid or semi-liquid lipid core at room temperature enveloped in a lipid envelope that is solid at room temperature, said gelled aqueous phase and nanocapsules containing at least one antibiotic, identical or different, the antibiotic in said aqueous phase being present in the form of a solute.

In particular, said hydrophilic polymeric gelling agent(s) is (are) chosen from $C_1$-$C_2$ carboxyalkylcelluloses having a viscosity greater than 1500 mPa·s, triblock copolymers consisting of poly(ethylene oxide) and poly(propylene oxide), triblock copolymers consisting of poly(ethylene glycol) and poly(lactic-co-glycolic acid), and mixtures thereof.

More particularly, triblock copolymers consisting of poly(ethylene oxide) and poly(propylene oxide) can be heat-sensitive and exhibit a lower critical solubility temperature (LCST) of between 15° C. and 40° C., and triblock copolymers consisting of poly(ethylene glycol) and poly(lactic-co-glycolic acid) can be heat-sensitive and exhibit a lower critical solubility temperature (LCST) of between 15° C. and 40° C.

Surprisingly, the inventors have thus observed that the formulation of specific lipid nanocapsules containing at least one antibiotic, in a gelled aqueous phase in accordance with the invention and itself loaded with antibiotic, proves to be very particularly advantageous.

Against all expectations, the packaging of the nanocapsules loaded with antibiotic, in a gelled aqueous phase is not detrimental on the one hand to the integrity of the nanocapsules during the storage of the pharmaceutical composition or to the in vivo release of the antibiotic contained in said nanocapsules.

A pharmaceutical composition in accordance with the invention is also found to be suitable for localized administration and therefore near or even in contact with an organ or in vivo implant. This is particularly useful for preventing and/or treating osteoarticular infections.

With regard to its viscosity, it can be easily taken and applied to sites that are infectious or likely to be infected or to the dedicated implant that will be or already is in contact with this site.

A pharmaceutical composition in accordance with the invention is suitable for formulating a high amount of antibiotic which is not accessible with only conventional lipid nanocapsules.

It also allows a controlled and in particular prolonged release of antibiotic insofar as it conveys one or both in two distinct modes, one directly in the gelled aqueous phase and the other in an encapsulated form in the gelled aqueous phase. This is particularly useful for the treatment and/or prevention of internal infections such as bone and joint infections. It is not necessary to carry out repeated administrations at short notice to ensure efficacy of the antibiotics. In particular, the compositions according to the invention make it possible to release the active ingredient constantly over a period of at least 14 days. After a period of 14 days, the antibiotic concentrations still present remain very high, exceeding by 50 to 100 times the Minimum Inhibitory Concentrations (MIC) of the bacteria generally at the origin of these infections.

The present invention further relates to an internal medical device dedicated to being handled in vivo and/or implanted in vivo and loaded with at least one pharmaceutical composition as defined according to the invention for its use for treating or preventing an infection, in particular a bacterial infection, in particular osteoarticular and affecting a joint or a bone, or developing in an implanted medical device.

This medical device considered can be directly an implant type device dedicated to being implanted, permanently or not, in vivo but also a dressing, compress or gauze dedicated to being placed in temporary contact with an internal organ or an implant for the purposes of treating or preventing a bacterial infection.

The present invention also relates to a pharmaceutical composition as defined according to the present invention, or an internal medical device as defined according to the invention, for their use, a targeted, local and prolonged delivery of the antibiotic(s) at an infection, in particular bacterial, preferably osteoarticular, affecting a joint or bone, or developing at an implanted medical device or at a site potentially subject to such an infection, in particular bacterial, preferably osteoarticular.

The present invention also relates to the use of a pharmaceutical composition as defined according to the present invention, or an internal medical device as defined according to the invention, for a targeted, local and prolonged delivery of the antibiotic(s) at an infection, in particular bacterial, preferably osteoarticular, affecting a joint or a bone, or developing at an implanted medical device or at a site potentially subject to such infection, in particular bacterial, preferably osteoarticular.

FIGURES

FIG. 1 represents the concentrations of daptomycin measured 4 days after treatment with a single dose of 200 mg of the composition according to the invention in a model of Methicillin-resistant *Staphylococcus aureus* (MRSA) rabbit osteomyelitis.

Figure 2:
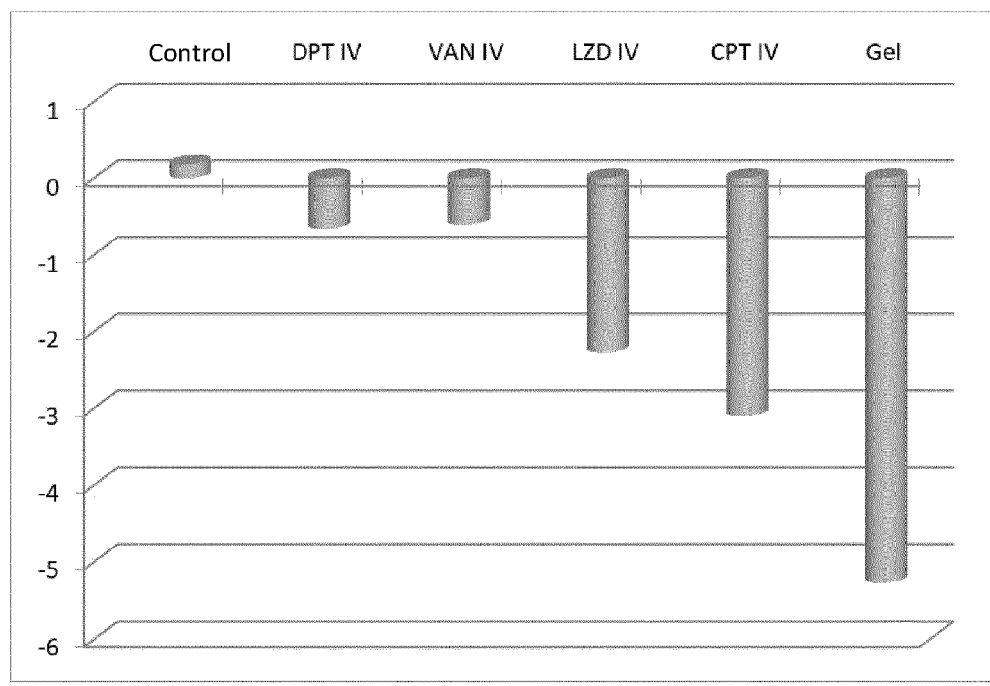

FIG. 2 represents the determination of the bacterial load ($\Delta \log_{10}$ CFU/g of tissue) at the bone 4 days after treatment with a single dose of 200 mg of the composition according to the invention in comparison with other antibiotics administered intravenously (IV) for 4 days in an experimental osteoarticular infection model in rabbits with MRSA (*$p<0.05$ versus control and other groups of antibiotics: LZD=Linezolid, DPT=Daptomycin, VAN=Vancomycin, CPT=Ceftarolin).

Figure 3:
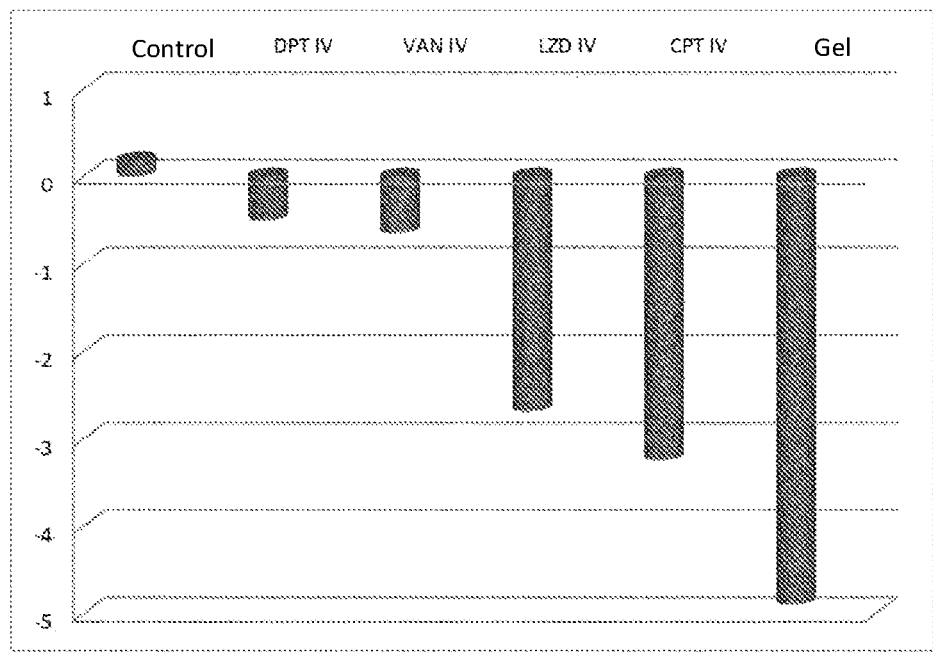

FIG. 3 represents the determination of the bacterial load ($\Delta \log_{10}$ CFU/g of tissue) in the bone marrow 4 days after treatment with a single dose of 200 mg of the composition according to the invention in comparison with other antibiotics administered intravenously (IV) for 4 days in an experimental osteoarticular infection model in rabbits with MRSA (*$p<0.05$ versus control and other groups of antibiotics: LZD=Linezolid, DPT=Daptomycin, VAN=Vancomycin, CPT=Ceftarolin).

Figure 4:
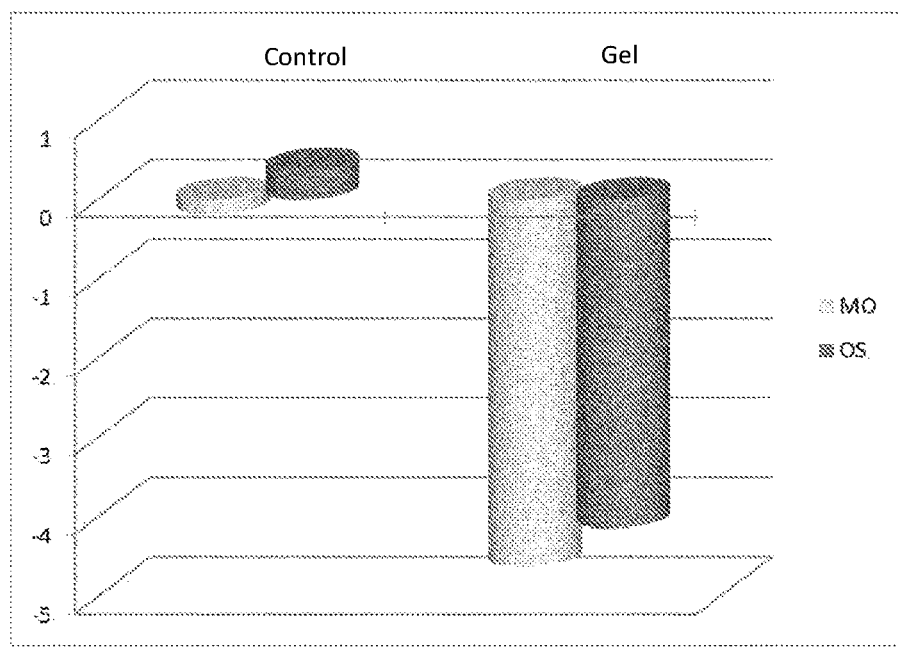

FIG. 4 represents the determination of the bacterial load ($\Delta \log_{10}$ CFU/g of tissue) at the bone marrow 14 days after treatment with a single dose of 200 mg of the composition according to the invention in comparison with an untreated group in an experimental osteoarticular infection model in rabbits with MRSA (*$p<0.05$) versus control.

Figure 5:
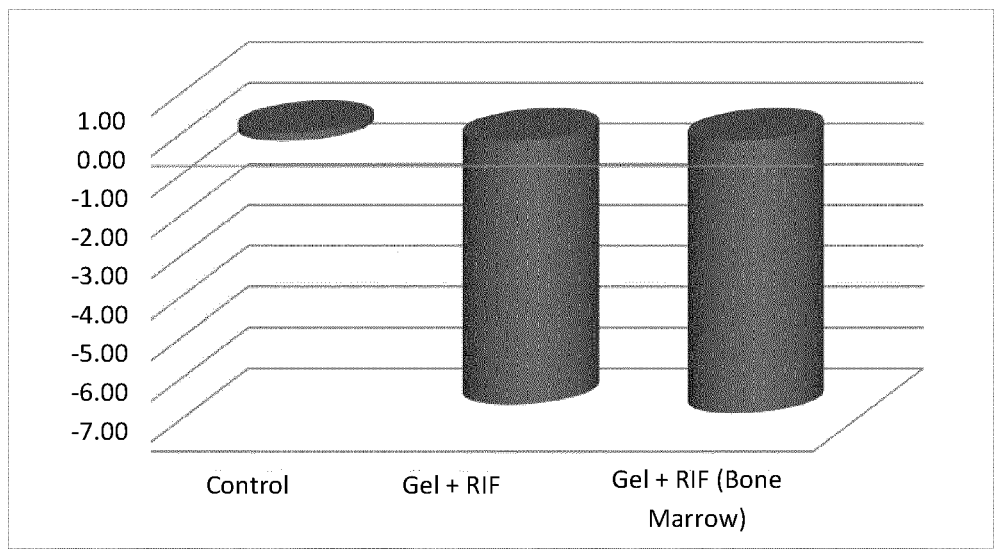

FIG. 5 represents the determination of the bacterial load ($\Delta \log_{10}$ CFU/g of tissue) at the bone marrow 4 days after treatment with a single dose of 200 mg of the composition according to the invention associated with rifampicin (RIF) administered intramuscularly (IM, 20 mg/kg every 12 hours, for 4 days), in an experimental osteoarticular infection model in rabbits with MRSA.

COMPOSITION

As stated above, a composition according to the invention is in the form of a gel at at least a temperature varying from 15° C. to 40° C. Thus a composition according to the invention is stabilized in a gelled state at a temperature varying at least from room temperature to body temperature.

In particular, a composition according to the invention has a viscosity between 15° C. and 40° C. greater than 10 Pa·s, preferably varying from 10 Pa·s to 10,000 Pa·s, more preferably from 50 to 1000 Pa·s.

This viscosity can be characterized at 25° C. with a shear rate of 0.01 s$^{-1}$, for example using a rheometer such as the one sold by the company Malvem under the name KINEXUS pro+.

This gelled appearance is mainly adjusted via the choice of the associated polymeric gelling agent.

However, it is clear that the concentration of the nanocapsules and of the active agent, in this case the antibiotic in its non-encapsulated form, will also contribute to the adjustment of this viscosity.

The gelled aqueous phase represents, for example, from 40% to 90% by weight, preferably from 45% to 85% by weight, relative to the total weight of the composition.

This gelled aqueous phase comprises at least one aqueous medium, a polymeric hydrophilic gelling agent, an active ingredient, preferably an antibiotic, and, where appropriate, a polyol distinct from said polymeric hydrophilic gelling agent.

a) Polymeric Hydrophilic Gelling Agent

As indicated above, the aqueous phase is gelled with at least one hydrophilic polymeric gelling agent.

Polymeric hydrophilic gelling agents are of course chosen for their compatibility with an in vivo use and their inertia vis-à-vis a part of the associated active ingredient but also nanocapsules.

Polymeric hydrophilic gelling agents chosen from $C_1$-$C_2$ carboxyalkylcelluloses having a viscosity greater than 1500 mPa·s, triblock copolymers consisting of poly(ethylene oxide) and poly(propylene oxide) are most particularly suitable for this reason, triblock copolymers consisting of poly(ethylene glycol) and poly(lactic-co-glycolic acid), and mixtures thereof.

More particularly, triblock copolymers composed of poly(ethylene oxide) and poly(propylene oxide) can be heat-sensitive and have a lower critical solubility temperature (LCST) of between 15° C. and 40° C., and the copolymers triblocks made of poly(ethylene glycol) and poly(lactic-co-glycolic acid) can be heat-sensitive and exhibit a lower critical solubility temperature (LCST) of between 15° C. and 40° C.

The carboxyalkylcelluloses suitable for the invention are water-soluble carboxymethylcelluloses, in particular carboxymethylcelluloses and their sodium salts.

High viscosity carboxymethylcelluloses (also called CMC HV) that is to say with a viscosity at least equal to 1500 mPa·s and in particular those sold by the company Sigma-Aldrich or under the trade name Calbiochem® by the company Merck Millipore and ultra high viscosity carboxymethylcelluloses (also called CMC ultra high viscosity) sold by the company Sigma-Aldrich are particularly suitable for the implementation of the invention.

Triblock copolymers consisting of poly(ethylene oxide) (PEO) and poly(propylene oxide) (PPO) suitable for the invention can be the copolymers of formula (PEO)x (PPO)y (PEO)z where x is between 5 and 200, y is between 5 and 100 and z is between 5 and 200.

Preferably, the values of x and z are the same.

The compounds in which x=106, y=69 and z=106 are very advantageously used.

Triblock copolymers particularly suitable for the implementation of the invention are liquid at 4° C. and gelled at 37° C. They are thus water-soluble and heat-sensitive. They preferably have a molecular weight of between 9500 and 15,000 g/mol, in particular between 9800 and 14,600 g/mol and more particularly between 9840 and 14600 g/mol and an ethylene oxide content of between 70.0% and 80.0%, in particular between 71.0% and 75.0%, and more particularly between 71.5% and 74.9%.

Triblock polymers consisting of poly(ethylene oxide) (PEO) and poly(propylene oxide) (PPO) sold under the name Pluronic® F127 (sold by the company Sigma Aldrich, CAS number 9003-11-6), Polaxamer® 407 or P407 (sold by the company BASF) or Pluronic® P123 sold by BASF are particularly suitable for the implementation of the invention.

Triblock copolymers consisting of poly(ethylene glycol) and of poly(lactic-co-glycolic acid) suitable for the invention are advantageously PEG-PLGA-PEG type triblock polymers, soluble in aqueous media and heat-sensitive.

According to a preferred embodiment, the hydrophilic polymeric gelling agents included in the gelled aqueous phase suitable for the present invention are chosen from $C_1$-$C_2$ carboxymethylcelluloses having a viscosity greater than 1500 mPa·s, preferably between 1500 mPa·s and 4500 mPa·s and/or poly (ethylene oxide) and poly (propylene oxide) triblock copolymers having a lower critical solubility temperature (LCST) of between 15° C. and 40° C.

Of course, the amount of polymeric gelling agent is adjusted to provide the expected viscosity of the composition according to the invention.

This adjustment is clearly within the competence of those skilled in the art.

In particular, a composition according to the invention can comprise from 1% to 30% by weight, preferably from 2% to 25% by weight of hydrophilic polymeric gelling agent(s), relative to the weight of the gelled aqueous phase.

According to a preferred variant, one composition according to the invention also contains a polyol.

b) Polyols

The term "polyol" is used to refer to organic molecules comprising at least two hydroxyl functions (—OH).

This polyol is distinct from hydroxylated polymers capable of being used as a gelling agent.

The presence of this polyol is very particularly advantageous for adjusting the pH of the composition and/or dissolving the various constituents.

Preferably, the polyol of the composition according to the invention has a saturated, branched or unbranched linear hydrocarbon chain.

Advantageously, the polyol comprises a number of carbon atoms ranging from 2 to 20, preferably from 2 to 12, even better from 5 to 12, and comprises from 2 to 12, better from 2 to 8, and even better from 2 to 6 hydroxyl functions.

The polyols of the composition according to the invention can be chosen from sorbitol (also called glucitol), mannitol, dulcitol, maltitol, isomaltitol (also called isomalt), xylitol, arabitol (also called lyxitol or still arabinitol), ribitol (also called adonitol), volemitol, and mixtures thereof, preferably sorbitol, mannitol, maltitol, and mixtures thereof, even better sorbitol.

According to a particularly preferred embodiment, the polyol is sorbitol.

A composition according to the invention can comprise from 1% to 30% by weight, preferably from 2% to 20% by weight, of polyol(s) relative to its total weight.

c) Aqueous Medium

As regards the aqueous medium, it is formed from water, optionally mixed with one or more water-soluble auxiliary solvents.

According to an alternative embodiment, this solvent medium is uniquely formed of water.

d) Lipid Nanocapsules

As specified above, a composition according to the invention also contains nanocapsules.

These nanocapsules are advantageously present in the gelled aqueous phase.

Advantageously, these nanocapsules can be present in a content varying from 2% to 90% by weight, or even from 5% to 85% by weight, or even from 10% to 80% by weight, or even from 10% to 70% by weight, relative to the total weight of the composition.

In particular, they can be used in a nanocapsules/gelled aqueous phase weight ratio varying from 10/90 to 50/50.

For the purposes of the present invention, the lipid nanocapsules suitable for the invention have an architecture distinct from micelles, reverse micelles or particles with liposome architecture.

More specifically, the lipid nanocapsules in accordance with the invention comprise a liquid or semi-liquid lipid core at room temperature, in which at least one lipophilic or hydrophilic antibiotic is incorporated, this core being surrounded (or enveloped) in a lipid envelope that is solid (therefore rigid) at room temperature.

The expression "at room temperature" means, in the context of the present invention, at a temperature between 15° C. and 25° C.

The expression "body temperature" means, in the context of the present invention, at a temperature between 35° C. and 38° C.

A "semi-liquid" medium should be understood as being a medium having a higher viscosity than a liquid medium. The "semi-liquid" medium is obtained by any suitable means, for example from the medium in liquid form, preferably by adding gelling agents. However, the semi-liquid medium can also consist of a compound or combination of compounds having an adequate viscosity in order to behave like a gel.

Preferably, the lipid nanocapsules suitable for the invention have a size of less than 100 nm, preferably of a size of between 10 nm and 50 nm, advantageously of between 17 nm and 25 nm. These sizes can be determined by dynamic light scattering, photon correlation spectroscopy, scanning electron microscopy, or transmission electron microscopy in cryoscopic mode.

Preferably, the nanocapsules suitable for the invention are those described and obtained according to the methods detailed in documents WO2001064328, WO2009004214, WO2009001019, WO2010067037 and WO2015118496.

According to a first variant, the lipid nanocapsules suitable for the present invention are nanocapsules known under the trade name of "Soludots" from the company CARLINA Technologies. They include a lipid core based on medium chain triglycerides, caprylic and/or capric acids, for example from Labrafac® WL 1349 from the company Gattefossé and/or Captex® 8000 from the company Abitec, which is a glycerol tricaprylate. The core is stabilized by a solid shell consisting of phospholipids, for example a lecithin (or a soya lecithin known under the name Lipoid S75-3, from the company Lipoid GmbH, comprising approximately 69% phosphatidylcholine and approximately 9% phosphatidyl. ethanolamine or even Lipoid S-100, from the company Lipoid GmbH) and a nonionic hydrophilic surfactant, such as polyethylene glycol stearate (polyethylene glycol-660 2-hydroxystearate marketed under the name Solutol® HS 15 (also called Kolliphor® HS 15) by BASF).

Preferably, the solid envelope enveloping the core of the lipid nanocapsules comprises, or essentially consists of, a lipophilic surfactant which is a phosphatidylcholine.

According to a second variant, the lipid nanocapsules suitable for the present invention are also "Soludots" as described above, but the lipid core of which also comprises an additive, a nonionic excipient dispersible in water, for example Labrasol® from the company Gattefossé, based on compounds of esters of PEG and a fraction of glycerides.

Preferably, for a lipophilic active ingredient and in particular a lipophilic antibiotic, the liquid or semi-liquid lipid core comprises, or essentially consists of, a fatty substance which is liquid or semi-liquid at room temperature, for example a triglyceride or a fatty acid ester or a mixture thereof.

More preferably, the liquid or semi-liquid lipid core of the lipid nanocapsules comprises, or essentially consists of, one or more triglycerides, one or more fatty acid esters, or one of their mixtures.

On the other hand, for a hydrophilic active ingredient and in particular a hydrophilic antibiotic, the active ingredient must be stabilized, at the lipid core, in the form of a reverse micellar system. Consequently, the liquid or semi-liquid lipid core comprises an oily phase comprising at least one fatty substance which is liquid or semi-liquid at room temperature, advantageously at least one triglyceride, a fatty acid ester, or a mixture thereof, and at least one surfactant.

Preferably, the encapsulated antibiotic(s) can represent up to 30% by weight of the lipid nanocapsules suitable for the invention, relative to the total weight of said lipid nanocapsules.

According to a preferred variant, lipid nanocapsules suitable for the invention comprise at least:
polyethylene glycol stearate, preferably polyethylene glycol-660 2-hydroxystearate;
glycerol tricaprylate;
sodium chloride;
a phospholipid chosen from lecithin, soya lecithin and mixtures thereof, preferably from soya lecithin and lecithin;
an antibiotic, and in particular daptomycin.

According to a more particularly preferred embodiment, the antibiotic included in the core of the lipid nanocapsules suitable for the invention is at least one daptomycin.

The lipid nanocapsules suitable for the invention can also comprise one or more other active ingredients distinct from the antibiotic(s) required according to the invention, for example a vitamin, an analgesic, an anti-inflammatory drug, a growth hormone, an antiseptic, a hemostat, and mixtures thereof.

e Antibiotics

When the term "antibiotic" is used in the present description without any further precision, this means that it can be just as well the antibiotic incorporated in the core of the nanocapsules as that included in the gelled aqueous phase.

A composition according to the invention can also be defined as comprising at least one free antibiotic and at least one encapsulated antibiotic.

The following are understood to mean:
"Free antibiotic" means the antibiotic not encapsulated in the nanocapsules and therefore conveyed directly in the gelled aqueous phase;
"Encapsulated antibiotic" means the antibiotic present only in the core of lipid nanocapsules.

A composition can comprise from 5% to 50% by weight of antibiotic(s), and preferably from 10% to 40% by weight of antibiotic(s), relative to its total weight.

The quantity of antibiotic(s) contained directly in the gelled aqueous phase (that is to say without taking into account that contained in the nanocapsules present in this same gelled aqueous phase) can in particular be at least 50 mg/ml, preferably between 50 and 500 mg/ml, more preferably between 75 and 400 mg/ml, even more preferably between 100 and 300 mg/ml, or even better between 125 and 250 mg/ml relative to the weight total of the gelled aqueous phase.

The amount of antibiotic(s) contained in the core of the nanocapsules can represent from 1% to 20% by weight, and preferably from 2% to 10% by weight, of the total weight of the nanocapsules.

An antibiotic suitable for the present invention can be chosen from:
lipopeptides, such as for example daptomycin,
glyco- or lipo-glycopeptides, such as for example vancomycin, telavancin, teicoplanin,
polypeptides, such as for example colistin,
rifamycins, such as, for example, rifampicin, rifabutin,
penicillins, such as for example penicillin G, penicillin V, amoxicillin, oxacillin, cephalosporins, such as, for example, ceflacor, cefalexin, cefuroxime, cefixime, penemes, such as for example imipenem, meropenem, doripenem, macrolides and related substances, such as, for example, erythromycin A, spiramycin, clarithromycin, roxithromycin, azithromycin, midecamycin, telithromycin, virginiamycin, pristinamycin, ansamycin, aminoglycosides, such as, for example, amikacin, gentamicin, tobramycin, quinolones and their fluorinated derivatives, such as for example ofloxacin, moxifloxacin, ciprofloxacin, levofloxacin, sulfonamides or sulfonamides, such as, for example, trimethoprim, sulfamethoxazole, fusidanines, such as fusidic acid, fosfomycin, oxazolidinones, such as linezolid, tedizolid, tetracyclines, such as for example doxycycline, lymecycline, methacycline, minocycline, and their mixtures.

More particularly, said antibiotic(s) is (are) chosen from daptomycin, rifampicin, vancomycin, colistin and mixtures thereof, and more preferably is at least daptomycin.

According to an alternative embodiment, said antibiotic or antibiotics included in the core of said lipid nanocapsules and in said gelled aqueous phase are identical.

According to a preferred embodiment variant, the core of said lipid nanocapsules on the one hand and said gelled aqueous phase on the other hand, both contain at least daptomycin.

According to another variant embodiment, said one or more antibiotics included in the core of said lipid nanocapsules and in said gelled aqueous phase are distinct.

Thus, the core of the lipid nanocapsules can comprise daptomycin and the antibiotic included in said gelled aqueous phase is different from daptomycin.

Likewise, the gelled aqueous phase can comprise daptomycin and the antibiotic included in the core of said lipid nanocapsules is different from daptomycin.

A pharmaceutical composition according to the invention can also simultaneously comprise lipid nanocapsules according to the invention comprising, as the single antibiotic, daptomycin and other lipid nanocapsules comprising at least one antibiotic distinct from daptomycin, in particular chosen from lipopeptides, lipoglycopeptides, polypeptides, rifamycins, penicillins, cephalosporins, carbapenems, macrolides, aminoglycosides, quinolones and their fluorinated derivatives, sulfonamides (or sulfonamides), oxazolidinones, fosfomycin, fusidic acid, tetracyclines, and mixtures thereof.

f) Other Components of the Composition

Of course, a pharmaceutical composition according to the invention can also comprise at least one active ingredient distinct from said antibiotic(s) required according to the invention.

This active agent can be present directly in the gelled aqueous phase and/or be present in the composition in a form encapsulated in nanocapsules distinct from those carrying said antibiotic.

For example, the additional active ingredient(s) can be chosen from vitamins, healing agents, minerals, analgesics, anti-inflammatory drugs, growth hormones, antiseptics, hemostats, and mixtures thereof.

The pharmaceutical composition according to the invention may also further comprise at least one pharmaceutically acceptable excipient and/or additive and/or solvent.

Pharmaceutically acceptable excipients and/or additives can in particular be chosen according to the mode of administration of the pharmaceutical composition.

Process for Preparing the Composition According to the Invention

A composition according to the invention can in particular be obtained by simple mixing of the nanocapsules in accordance with the invention with the other components required in the composition according to the invention. The order of introduction of the different components is not critical.

Another variant may be to form the aqueous phase beforehand by mixing liquid components in the aqueous medium and then introducing the nanocapsules therein.

Advantageously, the preparation of the composition can be carried out at a temperature of between 2° C. and 25° C.

As regards the nanocapsules, they can be prepared according to the protocols described in the examples and detailed in documents WO2001064328, WO2009004214, WO2009001019, WO2010067037 and WO2015118496.

Uses of a Composition According to the Invention

A pharmaceutical composition according to the invention is advantageously compatible with the various modes of administration usually considered in the therapeutic field.

It is in particular advantageously suitable for administration directly to the joint, bone, or implanted medical device. For example, it can be administered by injection in particular via a syringe but also by applying a deposit of composition to the surface of the targeted organ or of a device, implant or other, dedicated to being brought into contact with the organ.

Thus, the composition according to the invention is suitable for use in treating or preventing a bacterial osteoarticular infection affecting a joint or a bone, or developing in an implanted medical device.

The present invention also relates to internal medical devices comprising at least one pharmaceutical composition according to the invention.

"Medical device", within the meaning of the present invention, is the generic term designating any instrument, apparatus, equipment, material or other article, used alone or in combination, for therapeutic purposes, for the control, treatment or alleviation of an illness.

The term "internal medical device" is understood to mean a medical device suitable for direct application to the joint, bone, or implanted medical device.

The present invention also relates to an internal medical device according to the invention, for its use for treating or preventing an infection, in particular bacterial, preferably osteoarticular affecting a joint or a bone or developing at an implanted medical device, preferably said internal medical device then being represented by a dressing, a compress or a gauze.

An internal medical device according to the invention can in particular be an implant, prosthesis, screw, plate, dressing, compress or gauze.

The term "implant" or "prosthesis" can denote an element intended to be introduced and to remain in an organism for a more or less lengthy period. It may for example be an active implant (which requires a source of electrical energy to function), of an electronic chip, a bone segment, bone, prosthesis, including a visual prosthesis or a bone prosthesis, in particular of the hip or knee, a catheter, an implantable chamber.

As regards dressings, compresses or gauzes, they can in particular be dedicated to being brought into contact with a bone or joint for the purposes of preventing or treating an osteoarticular bacterial infection, but also in contact with an implanted internal device (i.e., prosthesis, implant, plate or screw).

For example, the pharmaceutical composition according to the invention can be applied to at least part of the surface of the dressing, compress or gauze, intended to come into contact with the infection site. However, it can also be incorporated within the dressing, compress or gauze, by any suitable means for diffusion to the infection site.

The association of a pharmaceutical composition according to the invention with the constituent material of an internal medical device according to the invention can be carried out before and/or simultaneously with the use or implantation in the body of said internal medical device.

The examples and figures which follow are presented by way of illustration and not limited to the field of the invention.

The expressions "between . . . and . . . ", "varying from . . . to . . . " and "ranging from . . . to . . . " must be understood with limits included, unless otherwise specified.

EXAMPLES

Example 1: Preparation of Nanocapsules Loaded with Daptomycin

We carry out 2.548 g of an emulsion containing 56 mg of Lipoid® S75-3 (Soya lecithin sold as Lipoid® S75-3 society Lipoid GmbH), 678 mg of lipophilic Captex® 8000 (glyceryl tricaprylate sold as Captex® 8000 Abitec), 1.547 g of Kolliphor® HS 15 (also known as Solutol® HS 15) from BASF, 71 mg of sodium chloride, 196 mg daptomycin and 1.64 g of 30% sorbitol solution in milli-Q water.

All of the above components are combined in the same beaker under magnetic stirring. Heating is applied until a temperature of 85° C. is reached. Still under magnetic stirring, the system is allowed to cool to a temperature of 60° C. This cycle (between 85° C. and 60° C.) is carried out until cancellation of the conductivity as a function of the temperature is observed. Phase inversion occurs after three cycles. At the last cooling, a quenching is carried out by throwing 12.5 ml of distilled water at 2° C.+/−1° C. on the mixture at 70° C. The system is then maintained under magnetic stirring for 5 min.

The particles obtained under the conditions described above, after three temperature cycles, have an average size of 43+/−7 nm. Their size polydispersity is 0.071. The size of the particles is measured by quasi-elastic light scattering ("Dynamic Light Scattering" or DLS). An average particle size of around 50 nm is measured. Furthermore, an observation made by atomic force microscopy in contact mode (Park Scientific Instruments apparatus, Geneva, Switzerland) shows that the nanocapsules are indeed solid at a temperature of 25° C.

Example 2: Preparation of a Composition According to the Invention

A triblock copolymer type polymeric gelling agent consisting of poly(ethylene oxide) and poly(propylene oxide) is used for these tests.

The nanocapsules in Example 1 are mixed with mechanical stirring at 50 rpm at 4° C., with 5.541 g of daptomycin, 1.64 g of a sorbitol solution at 0.3 mg/ml, 1.62 g of sorbitol solution 0.3 mg/ml in the quench water and 490 mg of Pluronic® F127 (BASF).

The viscosity of the composition of Example 2 was also evaluated at different shear rates, at room temperature (25° C.).

These characteristics are summarized in Table 1 below.

TABLE 1

| Example 2 | Value (Pa · s) |
|---|---|
| Viscosity of the composition (at a shear rate of 0.00 s$^{-1}$) | 4700 |
| Viscosity of the composition (at a shear rate of 0.01 s$^{-1}$) | 2500 |
| Viscosity of the composition (at a shear rate of 0.10 s$^{-1}$) | 950 |
| Viscosity of the composition (at a shear rate of 10.00 s$^{-1}$) | 400 |
| Viscosity of the composition (at a shear rate of 100.00 s$^{-1}$) | 70 |

The nanocapsules of Example 2 were further characterized in size (average diameter, polydispersity) by dynamic light scattering and their zeta potential was measured by electrokinetic methods. For carrying out the measurements, the suspensions of nanocapsules were prepared by diluting the formulas produced with ultra-pure water.

Table 2 charts their specific characteristics.

TABLE 2

| Hydrodynamic size of nanocapsules (nm) | 22.3 |
|---|---|
| Zeta potential of nanocapsules (mV) | −16.3 |

The degree of fillers of the composition obtained is determined by HPLC-UV assay of daptomycin. To do this, 50 mg of the composition were mixed with 9.46 ml of isopropanol, 4.151 ml of THF, 2.795 ml of 0.2 M PBS pH 5.5 and 3.225 ml of Milli-Q water. Then, the extract was filtered through a filter having a porosity of 0.22 μm and diluted with 0.2 M PBS pH 5.5 before injection into the HPLC-UV system. Table 3 below summarizes the results obtained.

TABLE 3

| | Appearance | Daptomycin concentration (mg/ml) of composition) |
|---|---|---|
| Example 2 | Yellow viscous solution | 192.00 +/− 4.55 |

Example 3: Preparation of a Composition According to the Invention

A carboxymethylcellulose polymer type polymeric gelling agent is used for these tests.

The nanocapsules of Example 1 are mixed with mechanical stirring using a U-shaped paddle at 200 rpm with 20.50 g of a sorbitol solution at 0.3 mg/ml, and 48.49 g of a sorbitol solution for dilution at 0.3 mg/ml is added. Ultra high viscosity carboxymethylcellulose, sold by the company Sigma-Aldrich, and daptomycin are introduced. The percentage of polymers relative to the mass of the aqueous phase is 3%. Thereafter, the heating is interrupted and the mechanical stirring maintained for 2 hours. The samples are stored at 4° C.

The composition thus obtained is opaque and yellow in appearance and has a daptomycin concentration of 187.55 mg/ml+/−2.76.

Example 4: In Vivo Efficacy Tests of a Composition According to the Invention

A dose of the composition according to Example 2 was injected into a model of Rabbit Osteomyelitis with MRSA by injection in situ. Tissue assays were performed using HPLC, in situ (bone and bone marrow) and in plasma, spleen, liver, kidneys and muscles 1 day, 4 days and 14 days after injection, to obtain the pharmacokinetics of daptomycin. A summary of the results (plasma, bone and OM) is presented in FIG. 1.

Daptomycin concentrations are very high 4 days after single administration, especially in bone and bone marrow. In addition, this concentration remains high even 14 days after injection.

In order to determine the bacterial load of the tissues, 1 ml of the composition according to Example 2 was injected in situ in an experimental model of IOA (osteoarticular infection) in a rabbit with MRSA (Meticillin-resistant *Staphylococcus aureus*) for a dose of 200 mg/ml of daptomycin (FIGS. 2, 3 and 4).

The bacterial loads in the two compartments (bone and bone marrow) were significantly reduced by injection of the composition according to the invention, 4 days and 14 days after injection, in comparison with other reference antibiotics at humanized doses (linezolid (LZD, 10 mg/kg/12 hours), Daptomycin (DPT, 6 mg/kg/day), 5 Vancomycin (VAN, 100 mg/kg/day in continuous infusion) and Ceftaroline (CPT, 10 mg/kg/12 hours) (p<0.001 versus controls, VAN, LZD, CPT and DPT).

Finally, the composition according to Example 2 was administered by local injection in combination with an antibiotic, rifampicin by the IM route at a dose of 20 mg/kg/12 hours.

A significant decrease (p<0.001 versus control) in the bacterial load in the two bone compartments (bone and bone marrow) is observed (FIG. 5).

The invention claimed is:

1. A pharmaceutical composition stabilized in a gelled state at at least a temperature varying from 15° C. to 40° C., comprising at least:
    an aqueous phase gelled with at least one hydrophilic polymeric gelling agent, said hydrophilic polymeric gelling agent(s) being present in an amount of between 2% and 25% by weight, relative to the weight of the gelled aqueous phase, said hydrophilic polymeric gelling agent(s) being chosen from carboxymethylcelluloses having a viscosity between 1500 mPa·s and 4500 mPa·s, and/or poly(ethylene oxide) and poly(propylene oxide) triblock copolymers having a lower critical solubility temperature (LCST) of between 15° C. and 40° C., said gelled aqueous phase further comprising at least one polyol, said polyol being sorbitol, said polyol(s) being present at least in an amount of between 1% and 30% by weight, relative to the total weight of the composition,
    lipid nanocapsules comprising a liquid or semi-liquid lipid core at room temperature enveloped in a lipid envelope that is solid at room temperature, said nanocapsules being present in an amount varying from 10% to 80% by weight, relative to the total weight of the composition,
    wherein said gelled aqueous phase and nanocapsules contain at least one antibiotic, identical or different, the antibiotic in said aqueous phase being present in the form of a solute, wherein said antibiotic(s) contained in the gelled aqueous phase being are present in an amount of at least 50 mg/ml, relative to the total weight of the gelled aqueous phase, and wherein said antibiotic(s) contained in the nanocapsules are contained in the core of the nanocapsules and are present in an amount of 1% to 20% by weight, relative to the total weight of the nanocapsules,
    wherein said antibiotic(s) is capable of being released constantly over a period of at least 14 days, and
    wherein the core of said nanocapsules and the gelled aqueous phase both comprising at least daptomycin.

2. The pharmaceutical composition according to claim 1, wherein the viscosity of the composition is greater than 10 Pa·s at a temperature varying from 15° C. to 40° C.

3. The pharmaceutical composition according to claim 1, wherein said polyol(s) is (are) present in an amount of between 2% and 20% by weight, relative to the total weight of the composition.

4. The pharmaceutical composition according to claim 1, wherein the liquid or semi-liquid lipid core of the lipid nanocapsules comprise, or consists essentially of, one or more triglycerides, one or more fatty acid esters, or mixtures thereof.

5. The pharmaceutical composition according to claim 1, wherein the solid shell enveloping the core of the lipid nanocapsules comprises, or consists essentially of, a lipophilic surfactant which is a phosphatidylcholine.

6. The pharmaceutical composition according to claim 1, wherein said lipid nanocapsules have a size less than 100 nm.

7. The pharmaceutical composition according to claim 1, wherein the nanocapsules are present in a content varying from 10% to 70% by weight, relative to the total weight of the composition.

8. The pharmaceutical composition according to claim 1, said composition being suitable for administration directly to the joint, bone, or implanted medical device.

9. The pharmaceutical composition according to claim 1, for its use in treating or preventing an osteoarticular bacterial infection affecting a joint or a bone, or developing in an implanted medical device.

10. An internal medical device comprising the pharmaceutical composition according to claim 1.

11. The internal medical device according to claim 10, said device being selected from an implant, prosthesis, screw, plate, dressing, compress or gauze.

12. The internal medical device according to claim 10, for its use for treating or preventing a bacterial infection affecting a joint or a bone, or developing in an implanted medical device, said internal medical device then being represented by a dressing, compress or gauze.

13. A method to treat an infection comprising administration of the pharmaceutical composition of claim 1 at a joint or a bone.

* * * * *